United States Patent [19]

Knöfel et al.

[11] Patent Number: 4,613,687
[45] Date of Patent: Sep. 23, 1986

[54] POLYISOCYANATES OF THE DIPHENYL METHANE SERIES

[75] Inventors: Hartmut Knöfel, Odenthal; Michael Brockelt, Berg.-Gladbach, both of Fed. Rep. of Germany

[73] Assignee: Bayer Aktiengesellschaft, Leverkusen, Fed. Rep. of Germany

[21] Appl. No.: 293,748

[22] Filed: Aug. 17, 1981

[30] Foreign Application Priority Data

Aug. 28, 1980 [DE] Fed. Rep. of Germany ....... 3032358

[51] Int. Cl.$^4$ ......................................... C07C 119/048
[52] U.S. Cl. .................................. 560/359; 560/347
[58] Field of Search ................ 260/453 AM, 453 PH; 560/359

[56] References Cited

U.S. PATENT DOCUMENTS

| | | | |
|---|---|---|---|
| 3,255,226 | 6/1966 | McShane, Jr. | 260/453 AM |
| 3,707,486 | 12/1972 | Oertel et al. | 260/389 |
| 3,903,124 | 9/1975 | Schnabel et al. | 260/453 AM |
| 3,933,701 | 1/1976 | Puig et al. | 260/2.5 AT |
| 3,941,822 | 3/1976 | Babiec, Jr. et al. | 260/453 P |

FOREIGN PATENT DOCUMENTS 1428578 3/1976 United Kingdom.

OTHER PUBLICATIONS

Siefken, Annalen der Chemie, vol. 562, p. 135 (1949).

*Primary Examiner*—Dolph H. Torrence
*Attorney, Agent, or Firm*—Gene Harsh; Joseph C. Gil; Lyndanne M. Whalen

[57] ABSTRACT

A polyisocyanate or mixture of polyisocyanates in which the main component(s) correspond to the formula:

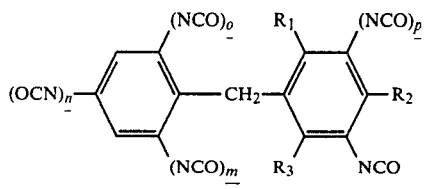

in which

R$_1$, R$_2$, and R$_3$ each represent hydrogen or a saturated alkyl group containing from 1 to 12 carbon atoms, provided that at least two of these radicals represent hydrogen; and m, n, o and p each represent 0 or 1, provided that when m, n, o and/or p represent 0, the free valency is taken up by a hydrogen atom and that the sum of m+n+o+p is greater than 1 on a statistical average.

Such polyisocyanate or mixture of polyisocyanates may be produced by first reacting a 4-nitrobenzyl halide, a 3-nitrobenzyl halide, a benzyl halide, a benzyl alcohol or a nitrobenzyl chloride isomer mixture with nitrobenzene, an alkyl-substituted nitrobenzene, an alkyl benzene or benzene in the presence of a Friedel-Crafts or an acid catalyst. This reaction product is then nitrated, the nitro groups are converted to amino groups by reduction or hydrogenation and the amino compound(s) subsequently phosgenated to form the polyisocyanate(s). The purity of the product polyisocyanate may be improved by distilling off secondary products before and/or after the phosgenation.

1 Claim, No Drawings

POLYISOCYANATES OF THE DIPHENYL METHANE SERIES

BACKGROUND OF THE INVENTION

This invention relates to polyisocyanates of the diphenyl methane series in which isocyanate groups in the 3,4'- and, optionally, in the 3,2'-positions are present. This invention also relates to processes for the production of such polyisocyanates.

Difunctional diisocyanato-toluene isomers (TDI) and difunctional diisocyanato-diphenyl methane isomers (particularly, 2,4'- and/or 4,4'-diisocyanato-diphenyl methane) are among the most important polyisocyanates in polyurethane chemistry, both technically and economically. Mixtures of higher polyisocyanates of the diphenyl methane series which may be obtained by the phosgenation of aniline/formaldehyde condensates are particularly important materials. These higher polyisocyanate mixtures of the diphenyl methane series, which on a statistical average have an NCO functionality of more than two, are particularly important as starting materials for the production of polyurethane foams. However, conventional mixtures of this type are disadvantageous because they are mixtures of distillable polyisocyanates of low functionality with non-distillable homologues of relatively high functionality. Any increase in NCO functionality of the entire mixture is obtained at the expense of an increase in the molecular size of the high functionality polyisocyanates and consequently an increase in the viscosity of the mixture. Another disadvantage of conventional diphenyl methane polyisocyanate mixtures of relatively high functionality is their tendency to undergo partial crystallization at low temperatures. Such crystallization makes it necessary to heat or chemically treat the mixture to liquefy it prior to use. Additionally, substantially pure polyisocyanates having an NCO functionality of three may be produced with considerable difficulty by the traditional methods. Although it is theoretically possible to separate trifunctional polyisocyanates from phosgenation products by distillation, considerable quantities of distillation residues accumulate which contain both polyisocyanates having a functionality of more than three and secondary products having carbodiimide and isocyanurate groups. Because of the high viscosity of such residues and the presence of undesirable secondary products, these distillation residues would be of limited value in the production of high-quality polyurethane plastics.

SUMMARY OF THE INVENTION

It is an object of the present invention to provide a new polyisocyanates of the diphenyl methane series in which isocyanate groups are present in the 3,4' positions.

It is another object of the present invention to provide a polyisocyanate or mixture of polyisocyanates having high isocyanate functionality which does not have an undesirably high viscosity.

It is a further object of the present invention to provide a polyisocyanate or mixture of polyisocyanates which need not be liquefied or chemically treated before being used in the production of polyurethanes.

It is yet another object of the present invention to provide a polyisocyanate or mixture of polyisocyanates having a high isocyanate functionality which is useful in the production of a significant amount of high-quality polyurethane plastics.

It is also an object of the present invention to provide processes for making a polyisocyanate or mixture of polyisocyanates which are particularly advantageous starting materials in the production of polyurethanes.

These and other objects which will be apparent to those in the art are accomplished by the polyisocyanate corresponding to the general formula:

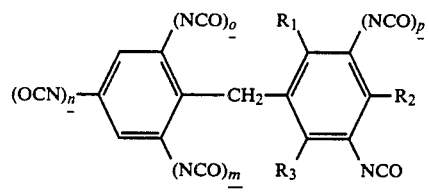

in which $R_1$, $R_2$, $R_3$, m, n, o and p are as defined below. Such polyisocyanates may be produced by reacting a 4-nitrobenzyl halide, a 3-nitrobenzyl halide, a benzyl halide, a benzyl alcohol or a nitrobenzyl chloride isomer mixture with nitrobenzene, alkyl-substituted nitrobenzenes, an alkyl benzene, or benzene in the presence of a catalyst as hereinafter described in more detail. This reaction product is then nitrated, the nitro groups are converted to amino groups by reduction or hydrogenation and the amino compound is phosgenated to form the polyisocyanate. The purity of the product polyisocyanate may be improved by distilling off secondary products before and/or after the phosgenation.

DETAILED DESCRIPTION OF THE INVENTION

The present invention relates to relatively pure polyisocyanates, polyisocyanates in which up to 40 wt. % (based on the mixture as a whole) may be other alkyl-substituted polyisocyanato-diphenyl methane isomers and mixtures of polyisocyanates corresponding to the following formula:

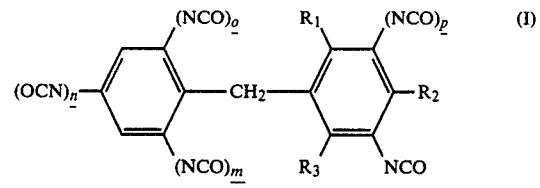

wherein each of the two aromatic rings contains at least one isocyanate group; and, wherein $R_1$, $R_2$ and $R_3$, each represent hydrogen or a saturated alkyl group containing from 1 to 12 carbon atoms (preferably a methyl or ethyl group) provided that at least two of the radicals $R_1$, $R_2$ and $R_3$ represent hydrogen; and m, n, o and p each represents 0 or 1; provided that when m, n, o and/or p represents 0, the free valency is saturated by a hydrogen atom and the sum of m+n+o+p is greater than 1 on a statistical average. These polyisocyanates are particularly useful in the production of polyurethane plastics by the isocyanate polyaddition process.

The present invention also relates in particular to polyisocyanates corresponding to the general formulae:

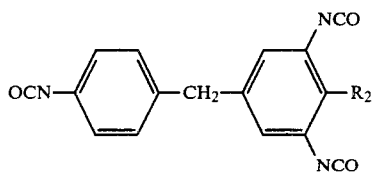

and

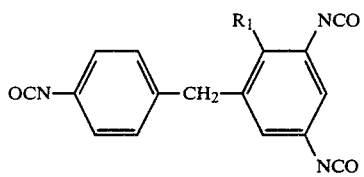

wherein $R_2$ represents hydrogen, a methyl group or an ethyl group; and $R_1$ represents a methyl group or an ethyl group.

These polyisocyanates are often present as the main component in the preferred polyisocyanate mixtures of the present invention but they may also be prepared in pure form.

The present invention also relates to processes described in detail below for the production of these polyisocyanates and polyisocyanate mixtures.

The compositions of the mixtures according to the present invention and the starting materials and intermediate products described herein are based on values which may be determined by gas chromatography.

The polyisocyanates or mixtures of polyisocyanates of the present invention are polyisocyanates of the diphenyl methane series containing an alkyl substituent having from 1 to 12 carbon atoms. The preferred alkyl-substituted compounds of the present invention are those in which the alkyl substituent contains 1 or 2 carbon atoms, i.e., is a methyl or ethyl radical.

In one process for producing the polyisocyanates or polyisocyanate mixtures of the present invention a 4-nitrobenzyl halide is reacted in the presence of a Friedel-Crafts catalyst with nitrobenzene and/or with 1-alkyl-2-nitrobenzene and/or with 1-alkyl-4-nitrobenzene and/or with technical mixtures of these alkyl nitrobenzene isomers in which the alkyl radicals contain from 1 to 12 carbon atoms to form dinitro compounds or mixtures of dinitro compounds corresponding to the general formula:

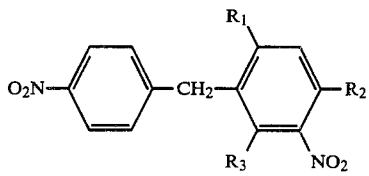

in which $R_1$, $R_2$ and $R_3$ are as defined above. The technical mixtures of alkyl nitrobenzene isomers used as reactant materials may include up to 15 wt. % (based on the total mixture) 1-alkyl-3-nitrobenzene. The product dinitro compounds may include up to 20 wt. % isomeric dinitro-diphenylene methanes. After this reaction, the product is freed from the catalyst. The reaction product thus-obtained is subjected to a nitration reaction to form nitro compounds corresponding to the general formula:

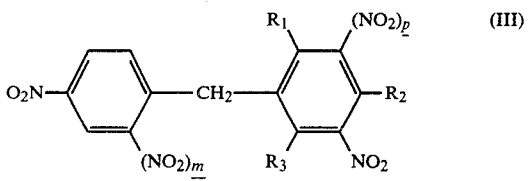

wherein $R_1$, $R_2$ and $R_3$ are as defined above; m and p each represent 0 or 1 provided that when m or p represents 0, the free valency is saturated by a hydrogen atom and the sum of m+p on a statistical average is greater than 0. The reaction product represented by formula (III) is then converted by hydrogenation or reduction of the nitro groups into the corresponding aromatic diamino compounds. These polyamino compounds are subsequently converted by phosgenation into the polyisocyanates. The content of triamino isomers in the polyamine mixtures may be increased by removing secondary products by distillation before the phosgenation reaction. The content of the triisocyanato isomer in the polyisocyanate mixtures may also be increased by distilling off secondary products boiling at lower or higher temperatures from the product of the phosgenation reaction.

As used herein, "nitrobenzyl halide" and "benzyl halide" are to be understood to include benzyl chlorides and bromides, particularly benzyl chlorides.

In the Friedel-Crafts condensation which takes place between 4-nitrobenzyl halide and nitrobenzene and/or 1-alkyl-2-nitrobenzene and/or 1-alkyl-4-nitrobenzene and/or technical mixtures of these isomers (which may include up to 15 wt. % based on the mixture as a whole, of 1-alkyl-3-nitrobenzene), the reactants may be used in quantities such that from 1.0 to 20 moles (preferably from 2 to 10 moles) of nitrobenzene and/or alkyl nitrobenzene are available for each mole of nitrobenzyl halide. The reactant used in excess also acts as solvent. The catalysts which may be used in this condensation reaction include the conventional Friedel-Crafts catalysts, such as aluminum chloride, iron chloride, titanium tetrachloride and tin tetrachloride. Iron trichloride is the preferred catalyst. The catalyst should generally be used in quantities of from 1 to 100 mole percent, preferably from 5 to 50 mole percent (based on the benzyl halide component). The Friedel-Crafts condensation reaction is generally carried out at a temperature of from room temperature to the boiling point of the reaction mixture, i.e., at a temperature of from about +20° to about 200° C. (preferably from 30° to 120° C.). After the condensation reaction, the catalyst is removed (preferably by washing with water and optionally dilute hydrochloric acid) and the excess unreacted starting material is distilled off.

The catalyst-free condensation product is then subjected to a nitration reaction in accordance with procedures known to those in the art. This nitration reaction may be carried out in the presence of a suitable solvent, such as methylene chloride. "Nitration acid", i.e., a mixture of concentrated sulfuric acid with nitric acid or, preferably, highly concentrated (approximately 98%) nitric acid, is used for nitration. This nitration acid is used in a quantity such that at least 0.1 mole, preferably from 0.1 to 2.1 moles, and most preferably from 0.2 to 1.2 moles of nitric acid are available for each mole of dinitro compound. When used in such quantities, at least 0.1, preferably from 0.1 to 1 more nitro group (on a statistical average) is introduced into the dinitro compound during nitration, thereby increasing the NO$_2$-functionality to more than 2, preferably from 2.1 to 3, and most preferably from 2.2 to 2.7. The nitration reaction is generally carried out at a temperature of from −20° to +100° C., preferably from +20° to +70° C. The organic phase present on completion of the nitration reaction is freed from the acid by phase separation, washing with water and a base, such as sodium carbonate solution. Then, any auxiliary solvent used is removed by distillation, optionally followed by the elimination of solvent residues by steam distillation.

The nitro groups present in this reaction product are then reduced into the corresponding aromatically bound amino groups. Reduction is preferably carried out by catalytic hydrogenation using a catalyst such as Raney nickel or palladium. The hydrogenation reaction is generally carried out in alcoholic solution. Methanol, ethanol and isopropanol are examples of solvents which may be used. The nitro compounds to be hydrogenated are generally used as a 10 to 50 wt. % solution. Hydrogenation may be carried out under pressure at a temperature of from 20° to 150° C., preferably from 30° to 110° C. Conversion of the nitro groups into the corresponding amino groups may also be carried out by known reduction processes by using reducing agents such as iron, zinc or tin. After the nitro group has been converted into the corresponding amino group, the catalyst is removed (e.g., by filtration) and the solvent is distilled off. If desired, the content of trifunctional polyamines in the polyamine mixture may be increased before phosgenation by distillation to remove secondary products boiling at lower or higher temperatures.

The polyamines or polyamine mixtures are then converted to the corresponding polyisocyanates by phosgenation in accordance with procedures known to those in the art. Chlorobenzene, dichlorobenzene or toluene, may be used as a solvent in this phosgenation. After the phosgenation reaction is complete, any auxiliary solvent is distilled off and the products of the present invention are left behind as residue. The content of triisocyanates in the products may be increased by distilling off secondary products which boil at lower or higher temperatures than the triisocyanates from the polyisocyanate-containing residue.

The above-described process as well as the processes described below of the present invention makes it possible to produce polyisocyanates or polyisocyanate mixtures in which the functionality of the products ultimately obtained may be varied over a wide range. The functionality of the product is determined by the degree of nitration and/or the removal of secondary products by distillation before and/or after phosgenation.

If the nitration reaction after the Friedel-Crafts condensation is carried out in such a way that on a statistical average one more mole of nitro groups is introduced per mole of dinitro compound, the main products formed in the above-described process are polyisocyanates or mixtures of polyisocyanates corresponding to general formula (I). Up to 40 wt. %, preferably up to 25 wt. % (based on total composition) of other, optionally alkyl-substituted triisocyanato-diphenyl methane isomers, may be present in these polyisocyanates or mixtures of polyisocyanates. It is preferred that one of the radicals R$_1$, R$_2$ or R$_3$ be a methyl or ethyl group and that the sum of m+n+o+p be 2. Such preferred compounds correspond to the general formulae:

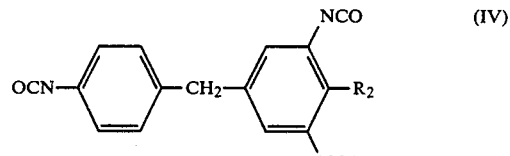

and

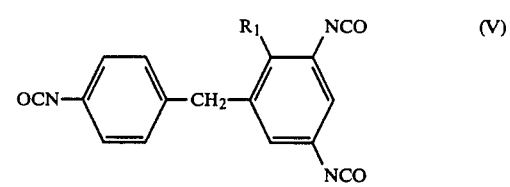

These compounds may be in admixture with the corresponding 3,2′,4′-triisocyanato isomers. The pure compounds corresponding to general formulae (IV) and (V) may be obtained, for example, by partial crystallization of the corresponding nitro compounds from a suitable solvent. Such solvents include ethyl acetate, ethanol, isopropanol and mixtures thereof. After such crystallization the pure trinitro compounds are converted to amino compounds which are then phosgenated in accordance with the above-described process according of the present invention. The triisocyanates corresponding to general formulae (IV) and (V) may be readily produced in pure form when the radicals R$_2$ and R$_1$ represent hydrogen, a methyl group or an ethyl group.

As has already been discussed, the functionality of the products of the present invention may be affected both by the degree of nitration and also by the removal of secondary products by distillation before and/or after phosgenation. It is therefore possible to produce alkyl-substituted polyisocyanates having the same NCO functionality yet different properties from the same starting materials by varying the degree of nitration and/or by distillation to remove secondary products. This variation in properties occurs when, for example, more than one isomer is present (even at the dinitro stage). If nitrobenzene or 1-alkyl-4-nitrobenzene is used as a starting material, such variation does not occur because substantially only one isomer is present at the dinitro stage. However, when 1-alkyl-2-nitrobenzene is reacted with the 4-nitrobenzyl halide, two isomers are present at the dinitro stage. Generally, different dinitro isomers show different reactivity on further nitration, with the result that, as nitration progresses, the composition of the remaining dinitro compounds continuously changes.

In a second process suitable for producing polyisocyanates or polyisocyanate mixtures according to the present invention, a 4-nitrobenzyl halide is reacted with an alkyl benzene containing from 1 to 12 carbon atoms in the alkyl radical in the presence of Friedel-Crafts catalysts to form a mixture of mononitro compounds corresponding to the general formula:

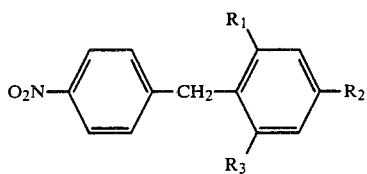

(VI)

wherein $R_1$, $R_2$ and $R_3$ are as defined below. The catalyst is then removed from the reaction product. Subsequently, the reaction product from the Friedel-Crafts condensation is subjected to a nitration reaction to form polynitro compounds corresponding to the general formula:

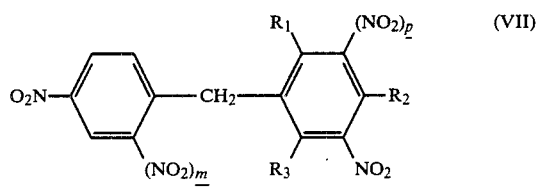

(VII)

wherein $R_1$, $R_2$ and $R_3$ each represent hydrogen, a methyl group or an ethyl group with one of these radicals representing a methyl or ethyl group and the other two radicals representing hydrogen; and m and p each represent 0 or 1 provided that when m or p represents 0, the free valency is saturated by a hydrogen atom and the sum of m+p on a statistical average is greater than 0. The polynitro compounds thus-obtained are then converted to the corresponding aromatic polyamine compounds by hydrogenation or reduction of the amino groups. These polyamino compounds are converted by phosgenation into the corresponding polyisocyanates. The content of triamino isomers in the polyamine mixtures may be increased by removing secondary products (e.g., by distillation) before the phosgenation reaction. The content of the corresponding triisocyanato isomer in the polyisocyanate mixtures may also be increased by the removal by distillation of secondary products boiling at lower or higher temperatures.

The first step of this second process corresponds to that of the first process described above with the exception that alkyl benzene rather than the nitrobenzenes or nitrobenzyl halides of the first process is used as the starting material. In this second process, the boiling temperature of the alkyl benzene which is used in excess represents the upper limit of the temperature range. The catalyst-free condensation product is then nitrated in known manner to form a mixture of isomeric polynitro compounds corresponding to general formula (VII). The nitration reaction may be carried out in the presence of a suitable solvent, such as methylene chloride, using "nitration acid", i.e., a mixture of concentrated sulfuric acid and nitric acid (preferably highly concentrated, approximately 98% nitric acid). The nitration acid is used in a quantity such that from about 1.1 to 3.1 moles (preferably from 1.2 to 2.2 moles) of nitric acid are available for each mole of mono-nitro compound, so that on a statistical average the nitration product contains more than 2, preferably from 2.1 to 3 nitro groups per molecule. The nitration reaction which is generally carried out at a temperature of from −20° to +100° C., preferably from 0° to 70° C., may be carried out in one or two stages. The acid present after the nitration reaction is then removed from the organic phase by phase separation. Such separation may be accomplished by washing with water and a solution such as a sodium bicarbonate solution. Any auxiliary solvent is then removed by distillation, optionally followed by the removal of solvent residues by steam distillation. The polynitro compounds are then converted to amino compounds and polyisocyanates in the same manner as in the first process described above.

In this second process, the polyisocyanate mixtures according to the present invention formed are generally mixtures containing from about 70 to 90 wt. % of di- and polyisocyanato-2-, -4- or -6-alkyl diphenyl methane and from 10 to 30 wt. % of other, analytically unidentified alkyl-substituted polyisocyanato-diphenyl methane isomers. The polyisocyanates produced by this process correspond substantially to the general formula:

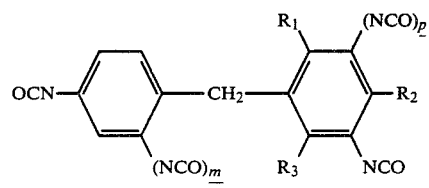

wherein $R_1$, $R_2$, $R_3$, m and p are as defined for formula (VII).

Polyisocyanates or polyisocyanate mixtures according to the present invention may be produced in a third process in which a 3-nitrobenzyl halide is reacted with benzene in the presence of Friedel-Crafts catalysts to form 3-nitro-diphenyl methane. The catalyst is removed from the reaction product upon completion of the reaction. The thus-obtained nitro compound is then subjected to a nitration reaction to form polynitro compounds corresponding to the general formula:

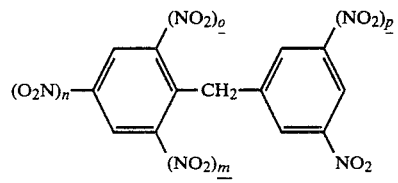

wherein m, n, o and p are as defined for general formula (I). These polynitro compounds are then converted into the corresponding aromatic polyamine compounds by hydrogenation or reduction of the nitro groups. The thus-produced polyamino compounds are subsequently converted by phosgenation into the corresponding polyisocyanates. As in the previously discussed processes, the content of triamine isomers in the polyamine mixtures may be increased by removal of secondary products before the phosgenation reaction. The content of the corresponding triisocyanato isomer in the polyisocyanate mixtures may also be increased by the removal by distillation of secondary products boiling at lower or higher temperatures.

Aside from the use of different starting materials, the third process according to the present invention corresponds entirely to the first two processes described above. In this third process and the processes described below, however, the mixtures accumulating as products may also contain (optionally alkyl-substituted) 3,5,2'-triisocyanatodiphenyl methanes (which would not be present in the products of the first two processes).

In a fourth process suitable for making the polyisocyanates of the present invention a technical nitro-benzyl chloride isomer mixture is reacted with an alkyl benzene containing from 1 to 12 carbon atoms in the alkyl radical in the presence of a Friedel-Crafts catalyst to form a condensate. A suitable technical nitrobenzyl chloride mixture may be obtained by the nitration of benzyl chloride. Such isomer mixture should contain from 10 to 50 wt. % (based on the mixture as a whole) of 2-nitrobenzyl chloride and from 50 to 90 wt. % (based on the mixture as a whole) of 4-nitrobenzyl chloride, in addition to minor amounts of 3-nitrobenzyl chloride. The Friedel-Crafts condensate thus formed contains mononitro compounds corresponding to the general formulae:

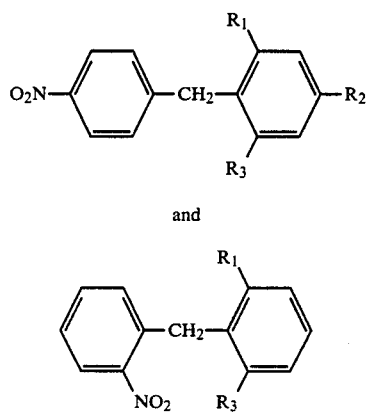

and wherein $R_1$, $R_2$ and $R_3$ are as defined above for formula (VII). The Friedel-Crafts catalyst is subsequently removed from the condensate. This condensate is then subjected to a nitration reaction to form a mixture of aromatic polynitro compounds containing nitro compounds corresponding to the general formula:

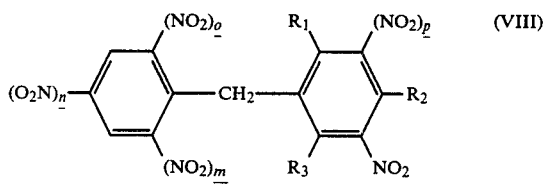

wherein each of the two aromatic rings contains at least one nitro group; $R_1$, $R_2$, $R_3$, m, n, o and p are as defined above for general formula (I) except that one of the radicals $R_1$, $R_2$, or $R_3$ must represent an alkyl radical. The nitro compounds thus-obtained are converted into the corresponding aromatic polyamines by hydrogenation or reduction of the nitro groups. These polyamines are subsequently converted by phosgenation into the corresponding polyisocyanates. The content of triamino isomers in the polyamine mixtures may be increased by removing secondary products (e.g., by distillation) before the phosgenation reaction. The content of the corresponding triisocyanato isomer in the polyisocyanate mixtures may also be increased by distillation to remove secondary products boiling at lower or higher temperatures.

This fourth process is carried out in the same way as the second process described above with the exception that instead of 4-nitrobenzyl halide, a technical nitrobenzyl chloride isomer mixture is used as the starting material. Appropriate isomer mixtures may contain from 10 to 50 wt. %, preferably from 30 to 40 wt. % of 2-nitrobenzyl chloride, from 50 to 90 wt. %, preferably from 50 to 60 wt. % of 4-nitrobenzyl chloride, and minor amounts of 3-nitrobenzyl chloride. "Minor amounts" as used herein are quantities of at most 20 wt. %, preferably at most 15 wt. % (based on the total weight).

This fourth process yields as the major product polyisocyanates corresponding to the general formula:

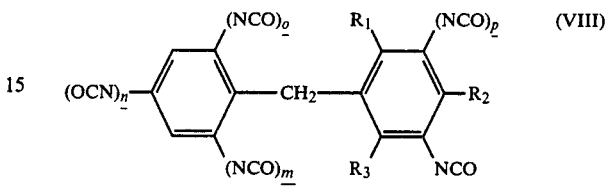

wherein $R_1$, $R_2$, $R_3$, m, n, o and p are as defined above for formula (VIII). Each of the two aromatic rings in the product contains at least one isocyanate group. The product mixture as a whole contains at least 60 wt. %, preferably at least 70 wt. % of these polyisocyanates. As mentioned above, the values of m, n, o and p may be adjusted (within the limits indicated) by the degree of nitration and/or by removal of secondary products by distillation at the amine or isocyanate stage.

In a fifth process according to the present invention a benzyl halide or benzyl alcohol is reacted in the presence of a Friedel-Crafts catalyst or an acid catalyst with an alkyl benzene containing from 1 to 12 carbon atoms in the alkyl radical to form a condensate. This condensate is made up of hydrocarbons corresponding to the general formula:

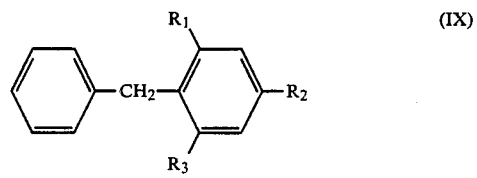

wherein one of the radicals $R_1$, $R_2$ or $R_3$ represents an alkyl group and the other two represent hydrogen. The alkyl diphenyl methane isomer mixture corresponding to general formula (IX) is then purified by distillation of the condensate and subjected to a nitration reaction. The nitration reaction is carried out to the extent that on a statistical average more than 2, preferably from 2.1 to 3, nitro groups are introduced for each hydrocarbon molecule. These polynitro compounds are then converted into the corresponding polyamines by hydrogenation or reduction of the nitro groups. The polyamines are subsequently converted into the corresponding polyisocyanates by phosgenation. As in the previously discussed processes, the content of triamino isomers in the polyamine mixtures may be increased by removing secondary products (e.g., by distillation) before the phosgenation reaction. The content of the corresponding triisocyanato isomer in the polyisocyanate mixtures may also be increased by the removal by distillation of secondary products boiling at lower or higher temperatures.

In the first step of this fifth process, an unsubstituted benzyl halide or benzyl alcohol is used instead of the nitro benzyl halide used in previously discussed processes.

Where a benzyl halide is used, the Friedel-Crafts condensation reaction conditions are the same as those of the first and second processes described above, including quantitative ratios between the reactants. However, it is preferred to use a molar ratio of alkyl benzene to benzyl chloride of from 5:1 to 20:1, with a molar ratio of from 8:1 to 15:1 being particularly preferred. In extreme cases, however, the condensation reaction may be carried out in the gas phase at temperatures of up to 300° C. However, the most preferred temperature for carrying out the Friedel-Crafts condensation lies at or below the boiling point of the alkyl benzene used.

Where benzyl alcohol is used as the starting material, the catalysts which may be used include a substantially involatile strong acid (such as sulfuric acid, aryl or alkyl sulfonic acid, phosphoric acid), a fixed-bed catalyst containing sulfonic acid groups (such as ion exchangers containing sulfonic acid groups)or an inorganic solid catalyst containing an acid center (e.g., Tonsils, zeolites, etc.).

When the Friedel-Crafts condensation is carried out with benzyl chloride and alkyl benzene, the quantitative ratios between the reactants are such that from 5 to 20 moles (preferably from 8 to 15 moles) of alkyl benzene are available for each mole of benzyl chloride, i.e., the alkyl benzene is used in excess. When benzyl chloride is used as the starting material the reaction temperature should generally be from $-20°$ to $+300°$ C., preferably from 20° to 110° C. The condensate that accumulates may be freed from the catalyst by washing out with water (in the case of homogeneous catalysis) or by filtration (in the case of heterogeneous catalysis). The excess alkyl benzene may be removed by distillation. This distillation also removes small quantities of condensates of higher molecular weight from the material to be nitrated.

In nitrating the Friedel-Crafts condensate in this fifth process, the condensate is treated in the same manner as the previously described processes with the exception that, in this process, the nitration acid is used in a quantity such that for each mole of hydrocarbon to be nitrated more than 2 moles (preferably from 2.2 to 3.2 moles) of nitric acid are available. Use of such quantities yields mixtures containing on a statistical average more than 2 (preferably from 2.1 to 3) nitro groups per molecule in the nitration products. The nitration reaction may be carried out in one or two stages. This means that the nitration acid may be delivered to the reaction mixture in portions. Where nitration is carried out in two stages, the residual acid accumulating in the second stage for introducing the second and any additional nitro groups may be reused in the first stage.

The thus-obtained alkyl-substituted dinitro-diphenyl methane isomers are further processed in the same manner as described above with respect to the first or second process. As has already been discussed above with respect to the first process, the 3,5,4'-triisocyanatodiphenyl methanes containing a methyl or ethyl substituent in the 2- or 4-position (which are particularly preferred materials) may be obtained by partial crystallization at the nitro stage before further treatment of the thus-obtained trinitro compounds to form the isocyanate.

In the fifth process suitable for the production of the polyisocyanates of the present invention, polyisocyanates corresponding to the general formula:

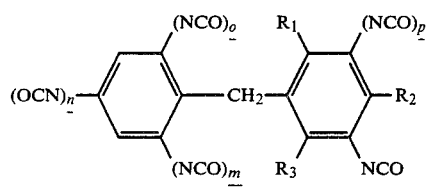

wherein each of the two aromatic rings contains at least one isocyanate group and the radicals $R_1$, $R_2$, $R_3$ and m, n, o and p are as defined above for formula (VIII). These polyisocyanates are generally obtained in admixture with up to 30 wt. % (based on the mixture as a whole) of other alkyl-substituted polyisocyanato-diphenyl methane isomers which cannot be fully identified by analysis.

The processes according to the present invention make it possible to produce new polyisocyanate mixtures of the diphenyl methane series in which the NCO functionality may be adapted over a wide range to suit the particular application envisaged. The NCO functionality may be adjusted both by the degree of nitration and also by distillation at the amine or isocyanate stage. As mentioned above in the description of the first process of the present invention, it is possible to produce polyisocyanates having the same functionality but different reactivity. The processes of the present invention make it possible to produce polyisocyanate mixtures which may have an average NCO functionality of greater than two and, in extreme cases, of greater than three without significantly increasing the average molecular weight of the polyisocyanates. The preferred mixtures of the present invention have an average NCO functionality of from 2.1 to 3, preferably from 2.2 to 2.7. Consequently, the sum of $m+n+o+p$ in the general formula for the mixtures of the present invention preferably amounts to from 1.1 to 2, most preferably from 1.2 to 1.7 (on average).

The polyisocyanate mixtures according to the present invention are characterized by a considerably lower viscosity than phosgenation products of aniline/formaldehyde condensates having the same average NCO functionality. The polyisocyanates or polyisocyanate mixtures of the present invention are also distinguished from the phosgenation products of aniline/formaldehyde condensates by their considerably reduced tendency to undergo partial crystallization at low temperatures. In the production of alkyl-substituted polyisocyanates or polyisocyanate mixtures according to the present invention, the properties of the products (particularly their suitability when used as a starting material in the production of polyurethanes) are unaffected by the position of the alkyl substituent or by the particular percentage content of the respective isomers distinguished by the position of the alkyl substituent. The mixtures of the present invention represent technical mixtures which often contain minor amounts, i.e., up to 30 wt. % of constituents which cannot be clearly identified by analysis (particularly by gas chromatography). These unidentified constituents are generally polyisocyanato-diphenyl methane isomers optionally containing an alkyl substituent in which two of the NCO groups are situated in the 2,4'-, 4,4'- or 3,3'-position, or mixture of such isomers. However, the presence of these secondary products in the mixtures according to the present invention within the quantitative limits indicated does not adversely affect the favorable properties of the primary product (i.e., the polyisocyanate constituting the component of the mixture present in the largest quantity). All of the polyisocyanates or polyisocyanate mixtures according to the present invention have the above-mentioned advantages over conventional phosgenation products of aniline/formaldehyde condensates. These polyisocyanates or polyisocyanate mixtures, particularly the preferred alkyl-substituted compounds, are particularly valuable starting materials for the production of polyurethane plastics. The new polyisocyanates or polyisocyanate mixtures according to the present invention may be used in any of the processes known to those in the art for the production of polyurethane plastics using either instead of or in admixture with conventional polyisocyanates (i.e., tolylene diisocyanates (TDI) and/or MDI).

Having thus described our invention, the following examples are given by way of illustration. The percentages given in these examples are weight percentages unless otherwise indicated.

EXAMPLES

EXAMPLE 1 (First process)

1(a) 171.6 g (1 mole) of 4-nitrobenzyl chloride were dissolved at room temperature in 755 g (5 moles) of 1-ethyl-2-nitrobenzene. 16.2 g (0.1 mole) of anhydrous iron(III) chloride were subsequently added. The reaction mixture was slowly heated with stirring to from 100° to 110° C. and maintained at that temperature until the evolution of hydrogen chloride had abated. The reaction was over after about five hours. After cooling the reaction mixture to room temperature, 500 ml of methylene chloride were added. The resulting mixture was then washed once with 200 ml of dilute hydrochloric acid and three times with 500 ml of water. After drying, first the methylene chloride and then the excess 1-ethyl-2-nitrobenzene were separated off.

According to gas chromatography, the residue (274 g) contained in its volatile fraction:
2 wt. % of 1-ethyl-2-nitrobenzene
3.8 wt. % of an unidentified dinitro compound
28.5 wt. % of 3,4'-dinitro-2-ethyl diphenyl methane
67.7 wt. % of 3,4'-dinitro-4-ethyl diphenyl methane.

1(b) 200 g (approximately 0.7 mole) of the crude mixture of 1(a) were dissolved in 400 ml of dichloromethane. Nitration acid consisting of a mixture of:
65 g (1.0 mole) of 98% $HNO_3$ and
100 g (1.0 mole) of 98% $H_2SO_4$ was then slowly added with stirring at 20° C. On completion of the addition, the mixture was stirred for about another 2 hours at from 28° to 30° C., after which the nitration acid was separated off. The remaining organic phase was washed twice with 200 ml of water, once with 2% sodium carbonate solution and twice more with water. The methylene chloride was then distilled off under normal pressure at a sump temperature of up to 90° C. and the solvent residues were removed using steam. The resulting product (220 g) was dehydrated under a water jet vacuum at 90° C./12 mm Hg.

1(c) 200 g of the crude product from 1(b) were dissolved in 600 ml of tetrahydrofuran, 30 g of fresh Raney nickel were added and the mixture was reduced using hydrogen at 50° C./100 bars until the pressure remained constant. On completion of the exothermic reaction, the reaction mixture was maintained at 80° C. for one hour under a hydrogen pressure of 100 bars. The pressure was then released, the catalyst was filtered off and the solvent and water were distilled off.

The residue (145 g) was distilled in an oil pump vacuum at 0.1 Torr. The first runnings (11 g) (80°-140° C.) were low-boiling compounds, mainly diamino-ethyl benzene. The main fraction (123 g) (140°-280° C.) was made up of:
0.4 wt. % of an unidentified diamino compound
4.6 wt. % of 2-ethyl-3,4'-diamino-diphenyl methane
22.6 wt. % of 4-ethyl-3,4'-diamino-diphenyl methane
20.2 wt. % of 2-methyl-3,5,4'-triamino-diphenyl methane and 4-ethyl-3,2,4'-triamino-diphenyl methane (not separated)
43.8 wt. % of 4-ethyl-3,5,4'-triamino-diphenyl methane
8.4 wt. % of higher boiling polyaryl amine residue (approximately 10 g).

1(d) 122 g of the distillate from 1(c) were dissolved in 1.25 liters of monochlorobenzene and the resulting solution was slowly added dropwise with stirring and cooling at 0° C. to a solution of 500 g of phosgene in 1 liter of monochlorobenzene. The reaction mixture was then slowly heated (while more phosgene was passed through) and refluxed for one hour. The monochlorobenzene was then distilled off under a water jet vacuum and the isocyanate distilled under further reduced pressure (0.4 Torr). After the first runnings of approximately 15 g (70° to 180° C.), 113 g distilled over at from 180° to 210° C. 38 g were left as distillation residue. According to GC-analysis, the distillate (main fraction) was made up of
22.3 wt. % of 2-nuclear diisocyanates and
77.2 wt. % of 2-nuclear triisocyanates.

This main fraction was then subjected to fine fractional distillation. The first fraction collected in this second distillation was 49 g (160°-175° C./0.2 Torr) made up of
34.9 wt. % 2-nuclear diisocyanate and
61.1 wt. % 2-nuclear triisocyanate.

The second fraction collected was 58 g (175°-178° C./0.2 Torr) of a colorless liquid (NCO content 39.4% by weight) made up of a mixture of 2-ethyl-3,5,4'-triisocyanato-diphenyl methane and 4-ethyl-3,5,4'-triisocyanato-diphenyl methane.

EXAMPLE 2 (First process)

2 (a) 343,0 g (2 moles) of 4-nitrobenzylchloride are admixed with 1370 g (10 moles) of p-nitrotoluene. The mixture is molten and admixed with 65 g (0,4 moles) of water-free iron (III) chloride.

The reaction mixture is slowly heated to 120° C. under stirring and maintained at this temperature until the formation of hydrogen chloride slows down. The reaction temperature is thereafter maintained for another hour at 120° C.

After cooling to room temperature the reaction mixture is dissolved in 1500 ml dichloromethane, the organic solution is thereafter extracted with 500 ml of half-concentrated aqueous hydrogen chloride solution and finally washed three times with 500 ml of water. Thereafter, the methylene chloride is distilled off.

The residue (approx. 450 g) is recrystallized with ethanol yielding 6-methyl-3,4'-dinitro-diphenylmethane of a 98% purity.

2 (b) 272 g (1 mole) of the purified dinitro-compound according to 2 (a) are dissolved in 1000 ml dichloromethane. A mixture of 150 g (1,5 mole) of 98% $H_2SO_4$ and 96 g (1,5 moles) 98% $HNO_3$ are added dropwise to this solution under stirring and external cooling at 25°–30° C. Subsequent to the addition of the acid the reaction mixture is stirred for three hours at 25°–30° C. The aqueous phase is separated from the organic phase. The organic phase is washed twice with 250 ml of water subsequently once with 250 ml of an aqueous solution of sodium carbonate (2% concentration) and finally again twice with 250 ml of water.

From this solution 500 ml of solvent are distilled off at normal pressure. The residue is then cooled to 0° C. The crystals which are thus formed are separated by filtration.

Yield: 146 g (44,6% of the theoretical)
Melting Point: 129°–131° C.,

According to GC-analysis the product contained 6,1% of dinitro-compound and 93,9% by weight of trinitromethyl-diphenyl-methane.

2 (c) 100 g of the nitro-compound according to 2 (b) are dissolved in 500 ml of tetrahydrofurane.

10 g of a Raney-nickel catalyst are added. The reaction mixture is exposed to hydrogen under a pressure of 50 bar and at a temperature of 50° C. until the hydrogen pressure remained constant. Subsequently a final hydrogenation is made by maintaining a hydrogen pressure of 100 bar at 100° C. for one hour. Subsequent to the removal of the catalyst of the solution thus obtained by filtration the solvent is distilled off. A residue consisting of 72 g of raw amine is obtained which, according to GC-analysis is composed of 4,8% by weight of 3,4'-diamino-6-methyldiphenylmethane
89,6% by weight of 3,5,4'-triamino-6-methyldiphenylmethane
and 5,6% by weight of 3,2',4'-triamino-6-methyldiphenylmethane.

The residue is distilled at 0,1 Torr. After first runnings (160°–210° C.) of 7 g a main fraction boiling at 210°–220° C. (53 g) is obtained which, (according to GC-analysis) is composed as follows:

<0,5% by weight of 3,4'-diamino-6-methyl-diphenylmethane
93,5% by weight of 3,5,4'-triamino-6-methyl-diphenylmethane
6,0% by weight of 3,2',4'-triamino-6-methyl-diphenylmethane.

2 (d) The main fraction according to 2 (c) is dissolved in 200 ml of dichloromethane. This solution is added dropwise under stirring at 0° C. to a solution of 200 g of phosgene in 1 l of monochlorobenzene. The reaction mixture was then slowly heated while more phosgene was passed through and refluxed for three hours. After removal of excess phosgene and of solvent under vacuum a residue (69 g) is obtained. This residue is extracted four times with 250 ml of n-hexane. Subsequent to the removal of the n-hexane of the combined extracts a residue (44 g ) is obtained as a yellowish oil which is distilled at 0,1 Torr. 40,5 g of a colourless oil having an NCO-content of 41,2% by weight is obtained which, according to GC-analysis, is composed as follows:

<1,0% by weight of 3,4'-diisocyanato-6-methyl-diphenyl-methane
5,8% by weight of 3,2',4'-triisocyanato-6-methyl-diphenyl-methane
93,3% by weight of 3,5,4'-triisocyanato-6-methyl-diphenyl-methane.

EXAMPLE 3 (Second process)

3 (a) 343 g (2 moles) of 4-nitrobenzylchloride are dissolved in 920 g (10 moles) of dry toluene and admixed with 32,4 g (0,2 moles) of water-free iron(III)-chloride.

The mixture is slowly heated under stirring to 80° C. maintained at this temperature for 5 hours and finally heated to reflux temperature after the evolution of hydrogen-chloride has come to a standstill. After cooling to room-temperature the reaction mixture is admixed with ice water. The organic phase is finally washed three times with 500 ml of water.

Working up of the toluene solution yielded 398,4 g (87,8% of the theoretical yield) of a low-viscous yellow oil boiling at 140°–150° C. at 0,5 Torr. The mixture consisted mainly of 2-, 3- and 4-methyl-4'-nitrodiphenyl-methane.

3 (b) 45,5 g (0,2 moles) of the distillate according to 3 (a) are admixed with 100 g of 83% $H_2SO_4$ at 20°–25° C. Under stirring and cooling a mixture of 40 g of 98% $H_2SO_4$ and 25,5 g of 98% $HNO_3$ are added dropwise at 20°–25° C. Sequently the reaction mixture is stirred for 20 minutes at 20°–25° C. The sulphuric acid is finally removed and the organic phase consisting essentially of the nitro-product is admixed with 150 ml of water. This mixture is then heated to reflux for one hour, cooled to approx. 85° C. and admixed with 100 ml of toluene. After the removal of the aqueous phase the organic phase is washed twice with a 3% aqueous solution of sodium carbonate (50 ml each) and twice with 50 ml of water. Toluene is removed under vacuum. The residue (54 g was hydrogenated according to Example 1 (c). Distillation of the amine mixture yielded at 0,1 Torr 30 g of a main fraction boiling at 180°–245° C. which, according to GC-analysis was composed as follows:

1,5% by weight of low-boiling amines
64,9% by weight of diamino-methyl-diphenylmethanes
33,4% by weight of triamino-methyl-diphenylmethanes.

The diamines consisted of 93% by weight of 2-,4- and 6-methyl-3,4'-diaminodiphenylmethanes and
7% by weight of other isomers.

3 (d) Phosgenation of the amine mixture according to 3 (c) and working up of the polyisocyanates thus obtained yields 28,5 g of a main fraction. This main fraction distills at 158°–200° C./0,1 Torr and exhibits and NCO-content of 34,5% by weight. It is composed of 73% by weight of diisocyanatomethyl-diphenylmethanes and
27% by weight of triisocyanatomethyl-diphenylmethanes.

EXAMPLE 4 (Second process)

4 (a) 171,5 g (1 mole) of 4-nitrobenzylchloride are dissolved in 263 g (2,5 moles) of 3-ethylbenzene. This solution is added at 40° C. under stirring to 3 g of water-free iron (III) chloride in 800 g (7,5 moles) of 3-ethyl-benzene.

The reaction mixture is heated to 80° C. and maintained at this temperature until the formation of hydrogenchloride has come to a standstill. Subsequently, the mixture is stirred for 2 hours at 70° C.–80° C. and worked up. 227 g (94,2% of the theoretical yield) of a low-viscous yellowish oil are finally obtained as main fraction boiling at 135°–145° C./0,1 Torr.

According to GC-analysis this oil was composed of

55% by weight of 2-(and 3-)ethyl-4'-nitrodiphenylmethane and

45% by weight of 4-ethyl-4'-nitrodiphenylmethane.

4 (b) 72,5 g of the isomer mixture according to 4 (a) are nitrated as described under 3 (b) using 100 g of 83% $H_2SO_4$ as solvent and a mixture of 60 g of 98% $H_2SO_4$ and 38,6 g of 98% $HNO_3$ as nitration acid. The reaction mixture was worked up as described under 3 (b). A raw nitration product (78 g) is obtained.

4(c) 75 g of the raw nitration product of 4 (b) are hydrogenated and worked up according to Example 1 (c). After working up of the reaction mixture 59,5 g of raw amine are obtained as main fraction which, according to GC-analysis, is composed as follows:

7% by weight of low-boiling amines

31% by weight of diamino-ethyl-diphenylmethanes and

62% by weight of triamino-ethyl-diphenylmethanes.

4 (d) 56 g of the raw product according to 4 (c) are phosgenated using 200 ml of methylenechloride as solvent. After working up of the phosgenation reaction mixture a main fraction (42 g) was obtained by distillation at 0,1–0,3 Torr boiling at 185°–205° C. and containing 36,5% of NCO. According to GC-analysis this fraction was composed of 34% by weight of diisocyanato-ethyl-diphenylmethanes and 66% by weight of triisocyanato-ethyl-diphenylmethanes.

EXAMPLE 5 (Third process)

5 (a) 171,5 g (1 mole) of 3-nitrobenzylchloride are dissolved in 546 g (7 moles) of 3-benzene. 13 g (0,1 moles) of water-free aluminium chloride are added.

The reaction mixture is slowly heated to reflux temperature. The formation of hydrogenchloride which started at 60° C. has come to standstill after one hour. The reaction mixture is then heated to reflux temperature for a further hour and finally cooled by admixing with ice water. The organic phase is washed three times with 500 ml of water.

Working up of the organic phase yielded 182 g (0,858 moles) of a main fraction boiling at 95°–135° C./0,1–0,5 Torr and which, according to GC-analysis contained 96% by weight, based on the total amount of the fraction, of 3-nitro-diphenylmethane.

213 g (1,0 mole) of 3-nitro-diphenylmethane obtained according to 5 (a) are dissolved in 200 ml of isododecane. A mixture of 150 g of 98% $H_2SO_4$ and 96 g of 98% $HNO_3$ is then added dropwise under stirring at 20°–30° C. The reaction mixture is stirred at room-temperature for one hour. The nitro-compounds which formed crystals are isolated by filtration, suspended in 500 ml of water and heated for one hour to reflux temperature of the water. Subsequently, 400 ml of toluene are added at 80°–90° C. The organic phase is separated from the aqueous phase and washed twice with 200 ml of a 3% aqueous solution of sodium carbonate and twice with 250 ml of water. After removal of the toluene 267 g of a raw material consisting of nitro-compounds are obtained.

According to GC-analysis the dinitro-portion of this raw material contained 10,8% by weight of 2,3'-dinitrodiphenylmethane 6,5% by weight of 3,3'-dinitrodiphenylmethane and 82,6% by weight of 3,4'-dinitrodiphenylmethane.

5 (c) The hydrogenation of the raw material according to 5 (b) yielded 173 g of a raw polyamine mixture.

163 g of a main fraction thereof boiled at 175°–250° C./0,1 Torr. This main fraction consisted of 78,4% by weight of diamino-diphenylmethanes, 18,5% by weight of triamino-diphenylmethanes, and 3,1% by weight of tetraminodiphenylmethane.

5 (d) The phosgenation of 162 g of the main fraction of 5 (c) and working up of the phosgenation reaction mixture 188 g of a main fraction boiling at 163°–205° C./0,3 Torr containing 35,4% by weight of NCO and consisting of 81,7% by weight of diisocyanatodiphenylmethanes and 18,3% by weight of triisocyanatodiphenylmethanes.

EXAMPLE 6 (Fourth process)

6(a) 254 g (2 moles) of benzyl chloride and 295 g (3 moles) of 98% sulfuric acid were introduced at −5° C. into 400 ml of methylene chloride. 190 g (3 moles) of 100% nitric acid were then added dropwise with stirring and cooling over a period of 1.5 hours at from −5° to 0° C. On completion of the addition, the mixture was stirred for another hour at 0° C. The nitration mixture was then stirred into 1.2 liters of ice water, the organic phase was separated off, washed twice with 500 ml of water, shaken with 300 ml of saturated sodium bicarbonate solution, washed once more with water and then dried over sodium sulfate. The methylene chloride was then distilled off under normal pressure. The residue was distilled under reduced pressure (0.1 Torr). 328 g of a mixture of mononitrobenzyl chlorides distilled over at a head temperature of from 80° to 120° C. The distillation residue weighed 6 g. In view of this small amount, distillation was dispensed with in further runs.

257.3 g (1.5 moles) of the thus-prepared nitrobenzyl chloride isomer mixture were taken up in 690 g (7.5 moles) of dry toluene. A solution of 31 g (0.2 mole) of anhydrous iron(III)chloride in nitromethane (70 ml of solution) was then added dropwise with stirring over a period of two hours at room temperature, followed by stirring for another twenty hours during which the temperature was maintained at from 20° to 25° C. (RT). The dark reaction solution was then poured into water, filtered and, after separation, the organic phase was washed until it showed a neutral reaction. The toluene solution was then stirred with solid $NaHCO_3$ and Fuller's Earth, filtered and concentrated. The gross yield amounted to 320 g (=94% of the theoretical yield).

According to GC-analysis, more than 97% of the product was made up of an isomer mixture of the methyl-mononitro-diphenyl methanes having methyl groups, predominantly in the 4- or 2-position.

6 (b) 227 g (1.0 mole) of the crude product from 2(a) were taken up in 400 ml of methylene chloride. Nitration acid consisting of a mixture of:

142 g (2.2 moles) of 98% $HNO_3$ and 220 g (2.2 moles) of 98% $H_2SO_4$ was then slowly added with stirring and cooling at 20° C. On completion of the addition, the mixture was stirred for a total of 5.5 hours (1 hour at 20° C., 2 hours at 30° C. and 2.5 hours at 40° C.). The nitration acid was then separated off and the organic phase was worked up in the same way as in Example 1(b). The residue weighed 287 g.

6(c) 250 g of the residue from stage 2(b) were taken up in 600 ml of methanol and reduced as in Example 1(c) following the addition of 20 g of Raney nickel B. Working up left 180 g of residue which was distilled at 0.1 Torr.

After first runnings of 8 g (110°-140° C.), the main fraction (151 g) distilled over at from 140° to 280° C. A residue of 16 g was left over.

Analysis of the main fraction by gas chromatography indicated the following composition:

≈1.6 wt. % low-boiling amines (TDA)
≈31.0 wt. % binuclear diamines
≈60.0 wt. % binuclear triamines
≈8.0 wt. % higher boiling amines
≈75 wt. % diamines and triamines made up of compounds containing (i) at least one amino group on each aromatic ring; (ii) amino groups situated in the 2- and/or 4-position of the non-methyl-substituted ring or in the 3- and/or 5-position of the methyl-substituted ring; and (iii) methyl substituents arranged in the 2-, 4- or 6-position.

6 (d) The main fraction (150 g) from 2(c) was dissolved in 1.5 liters of monochlorobenzene and the resulting solution was slowly added dropwise with stirring and cooling at 0° C. to a solution of 500 g of phosgene in 1.5 liters of monochlorobenzene. The reaction mixture was then slowly heated while more phosgene was passed through and refluxed for one hour. The monochlorobenzene was then distilled off under a water jet vacuum and the isocyanate distilled under further reduced pressure (0.1 Torr). After first runnings of approximately 10 ml, 156 g of isocyanate mixture made up solely of diisocyanates and triisocyanates distilled over at from 145° to 180° C. 35 g were left as distillation residue. The product isocyanate mixture had an NCO content of 37 wt. % (functionality 2.65).

EXAMPLE 7 (Fifth process)

7(a) 20 g of anhydrous iron(III) chloride were added under nitrogen to 18.4 kg (200 moles) of dry toluene. 2.53 kg of benzyl chloride were then added dropwise with stirring at from 20° to 25° C. Gaseous hydrogen chloride was given off. On completion of the addition, the mixture was stirred for 30 minutes, cooled and washed three times with 5 liters of water until the mixture was free from acid. The excess toluene was then separated off from the organic phase by distillation under normal pressure at a sump temperature of up to 150° C.

The residual hydrocarbon mixture (approximately 3.5 kg) was made up of:

≈90 wt. % 2-nuclear isomers
≈10 wt. % polynuclear isomers.

The binuclear fraction (approximately 3.15 kg; 78°-80° C./0.1 Torr) was first separated off by distillation under reduced pressure, after which the trinuclear fraction (280 g; 150°-175° C./0.1 Torr) was distilled.

According to GC, the binuclear fraction was made up of 40 to 42 wt. % 2-methyl diphenyl methane
4 to 5 wt. % 3-methyl diphenyl methane
54 to 56 wt. % 4-methyl diphenyl methane.

7(b) 1638 g (9 moles) of the mixture of binuclear isomers obtained in accordance with 3(a) were initially introduced at room temperature into 3600 ml of methylene chloride. Nitration acid consisting of 1160 g (18 moles) of 98% HNO₃ and
1800 g (18 moles) of 98% H₂SO₄ was added with stirring and cooling at from 25° to 30° C. On completion of the addition, the mixture was stirred for 15 minutes, after which the nitration acid was separated off. More nitration acid consisting of 675 g (10.5 moles) of 98% HNO₃ and
2100 g (21 moles) of 98% H₂SO₄ was then added dropwise to the organic phase at from 10° to 20° C., followed by stirring overnight at room temperature.

After the organic phase had been separated off, the product was washed twice with 1.25 liters of water, once with 5% sodium carbonate solution and twice more with water. The methylene chloride was then distilled off under normal pressure at a sump temperature of 90° C. and the solvent residues were removed using steam under a water jet vacuum at 80° C. The residue amounted to 2564 g of nitro product.

7 (c) 500 g of the crude product from the nitration stage of 3(b) were taken up in a mixture of 500 ml of methanol and 500 g of toluene. 50 g of fresh Raney nickel (iron content 15 wt. %) and 2 g of solid sodium carbonate were then added and the mixture was reduced at 50° C. under a hydrogen pressure of 100 bars. After the exothermic reaction was over, the hydrogen pressure was maintained at 100 bars for one hour at 100° C. The pressure was then released, the catalyst filtered off and methanol and water distilled off. The residue (392 g) was then distilled under a pressure of from 0.1 to 0.2 Torr at a sump temperature of 300° C. 366 g of distillate and 22 g of residue were obtained.

According to GC-analysis, the distillate contained (average value from four batches):

8.6 wt. % low-boiling amines
65.8 wt. % binuclear diamines
25.6 wt. % binuclear triamines.

7 (d) 500 g of the amine mixture (distillate) from 3(c) were dissolved in 2.5 liters of monochlorobenzene at from 35° to 40° C. and the resulting solution was slowly added dropwise with stirring and cooling at 0° C. to a solution of 1.25 kg of phosgene in 2.5 liters of monochlorobenzene. The reaction mixture was slowly heated while more phosgene was passed through until the monochlorobenzene boiled under reflux and then refluxed for one hour. After the monochlorobenzene had been distilled off under a water jet vacuum, the residue was rapidly distilled under a reduced pressure of 0.1 Torr. The yield amounted to 599 g of distillate and a residue of approximately 75 g.

The crude distillate was then subjected to slow fractional distillation (70 g fractions) in a 10 cm long column. The individual fractions are described in the following Table. After first runnings which, in addition to low-boiling isocyanates from secondary reactions, contained from about 25 to 30 wt. % methyl-diisocyanato-diphenyl methane, the NCO content began to increase from fraction 4 onward due to increased content of triisocyanates. The triisocyanates collected in the last fraction distilled over in substantially pure form.

| Fraction | | Temp./Pressure | NCO content (wt. %) | Functionality |
|---|---|---|---|---|
| FR* | (70 g) | 91–155° C./0.1 Torr | | |
| 1 | (70 g) | 155 | 31.8 | 2.0 |
| 2 | (70 g) | — | 31.7 | 2.0 |
| 3 | (70 g) | 170° C./0.1 Torr | 31.7 | 2.0 |

-continued

| Fraction | | Temp./Pressure | NCO content (wt. %) | Functionality |
|---|---|---|---|---|
| 4 | (70 g) | 170–175° C./0.1 Torr | 32.0 | 2.0 |
| 5 | (70 g) | 176–180° C./0.1 Torr | 36.1 | 2.5 |
| 6 | (70 g) | 180–190° C./0.1 Torr | 39.7 | 2.8 |
| 7 | (58 g) | 190–205° C./0.1 Torr | 41.2 | 3.0 |
| Residue | (11 g) | | | |

*FR = first runnings

EXAMPLE 8 (Fifth process)

8(a) The procedure described in Example 3(a) was repeated.

8(b) 910 g (5 moles) of the mixture of binuclear isomers of methyl diphenyl methane obtained in accordance with Example 3(a) were introduced into 2000 ml of methylene chloride at from 0° to 10° C. Nitration acid consisting of a mixture of 710 g (11.0 moles) of 98% HNO$_3$ and
1100 g (11.0 moles) of 98% H$_2$SO$_4$ was added with stirring and cooling at that temperature. On completion of the addition, the mixture was stirred for 30 minutes at 10° C., after which the nitration acid was separated off. The organic phase was washed twice with 1000 ml of water, once with 5% sodium carbonate solution and twice more with water. The methylene chloride was then distilled off under normal pressure at a sump temperature of up to 90° C., after which the solvent residues were freed from water using steam under a water jet vacuum at 80° C. The residue (1290 g) contained:

7–8 wt. % nitrotoluene
<1 wt. % mononitro-methyl diphenyl methane
92.6 wt. % dinitro-methyl diphenyl methane
<1 wt. % tri- and tetranitro-methyl diphenyl methane.

The dinitro fraction was approximately 18 wt. % dinitrated 2-, 4- or 6-methyl diphenyl methanes having nitro groups in the 3,2'-position; approximately 55 wt. % corresponding 3,4'-dinitro compounds; and approximately 27 wt. % other isomers.

1000 g of the crude mixture of nitro compounds obtained in accordance with 4(b) were stirred with 1 liter of ethanol at room temperature to form a crystal sludge which was then filtered under suction. The residue was then recrystallized once from isopropanol. The residue of the crystallization step (250 g=0.92 mole) was 3,4'-dinitro-4-methyl diphenyl methane which was approximately 98% pure (Mp. 146°–147° C.).

136 g (0.5 mole) of 4-methyl-3,4'-dinitro-diphenyl methane was re-reacted as in Example 1(b) with nitration acid consisting of 37 g (0.57 mole) of 98% HNO$_3$ and
57 g (0.57 mole) of 98% H$_2$SO$_4$ in 300 ml of methylene chloride at 20° C. On completion of the addition made at from 25° to 30° C., the reaction product was worked up in the same way as in Example 1(b). A residue of 154 g was produced.

8 (c) 150 g of the residue from 4(c) were introduced to the amino compounds and worked up in the same way as in Example 1(c). The gross yield amounted to 101 g. The crude product was then distilled under an oil pump vacuum of 0.1 Torr. After first runnings of approximately 5 g, which consisted of low-boiling compounds, a main fraction of 86 g was collected at from 140° to 280° C. A residue of 10 g was left behind in the distillation flask.

According to gas chromatography, the main fraction was made up of:

3.6 wt. % 2,4-diamino toluene
34.5 wt. % 4-methyl-3,4'-diamino diphenyl methane
3.1 wt. % 4-methyl-3,2,4'-triamino-diphenyl methane
57.1 wt. % 4-methyl-3,5,4'-triamino-diphenyl methane
<2 wt. % higher boiling amine compounds.

8 (d) The distillate from 4(d) (85 g) was reacted with phosgene and worked up in the same manner as in Example 1(d). The crude isocyanate (103 g) was separated by distillation at 0.4 Torr into

| | |
|---|---|
| First runnings (70–155° C.): | 10.3 g |
| Main fraction (155–180° C.): | 83.6 g |
| Residue: | 7 g |

According to analysis by gas chromatrography, the main fraction was made up of:

40.0 wt. % 2-nuclear diisocyanate
57.5 wt. % 2-nuclear triisocyanate.

This main fraction was separated by fractional distillation into fraction 1 (155°–175° C./0.2 Torr): 51.3 g
fraction 2 (175°–176° C./0.2 Torr): 26.4 g.

According to analysis by gas chromatography, fraction 1 was:

50 wt. % 4-methyl-3,4'-diisocyanato-diphenyl methane and
50 wt. % 4-methyl,3,5,4'-triisocyanate-diphenyl methane.

According to analysis by gas chromatography, fraction 2 was:

>99 wt. % 4-methyl-3,5,4'-triisocyanato-diphenyl methane (pale yellow needles, Mp. 70° C., NCO content 41.2% by weight).

EXAMPLE 9 (Fifth process)

9 (a) As Example 7 (a).

9 (b) 1547 g of the isomer mixture according to 9 (a) are nitrated using 1400 ml of 83% sulfuric acid as solvent and a mixture of 2125 g of 98% H$_2$SO$_4$ and 1365 g of 98% HNO$_3$ as nitration acid. The nitration was started at 28°–30° C. and finally at 100° C. Working up of the nitration reaction mixture yielded 2200 g of raw nitration product.

9 (c) 200 g of the raw nitration product of 9 (b) are hydrogenated to yield 147 g of a polyamine main fraction which was composed of 1.1% by weight of aminotoluene,
4,4% by weight of diaminotoluene,
74,8% by weight of diamino-methyl-diphenylmethane and
19,7 g of triamino-methyl-diphenylmethane.

9 (d) 145 g of the raw amine according to 9 (c) wasphosgenated to yield 182 g of a raw polyisocyanate mixture. 161 g of a main fraction boiling at 150°–205° C./0,1 Torr were isolated by distillation from this raw material. The main fraction contained 33,9% by weight of NCO and was composed of 78% by weight of diisocyanato-diphenylmethanes and 22% by weight of triisocyanato-diphenylmethanes.

What is claimed is:

1. A composition consisting essentially of at least 60 percent of a mixture of polyisocyanates corresponding to the general formula

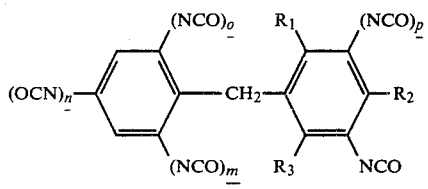

wherein each of the two aromatic rings contains at least one isocyanate group;

$R_1$, $R_2$ and $R_3$ which may be the same or different, each represent hydrogen, a methyl or an ethyl group, provided that two of the radicals $R_1$, $R_2$ and $R_3$ represent hydrogen; and m, n, o and p each represent 0 or 1 and that when m and/or n and/or o and/or p represents 0, the free valency is filled by hydrogen and that the sum of m+n+o+p is on a statistical average from 1.2 to 1.7 and up to 40 wt. % (based on the total composition) of other alkyl-substituted polyisocyanato-diphenylmethane isomers.

* * * * *